US010132251B2

(12) United States Patent
Park et al.

(10) Patent No.: US 10,132,251 B2
(45) Date of Patent: Nov. 20, 2018

(54) FUEL SENSOR FOR A VARIABLE-BLEND NATURAL GAS APPLIANCE USING THE WOBBE INDEX

(71) Applicant: The Regents of the University of California, Oakland, CA (US)

(72) Inventors: Chan Seung Park, Yorba Linda, CA (US); Partho Sarothi Roy, Riverside, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/289,915

(22) Filed: Oct. 10, 2016

(65) Prior Publication Data

US 2017/0101947 A1 Apr. 13, 2017

Related U.S. Application Data

(60) Provisional application No. 62/239,808, filed on Oct. 9, 2015.

(51) Int. Cl.
| | |
|---|---|
| *F02D 41/26* | (2006.01) |
| *F02D 41/00* | (2006.01) |
| *G01N 33/22* | (2006.01) |
| *B60K 15/03* | (2006.01) |
| *B60H 1/22* | (2006.01) |

(52) U.S. Cl.
CPC ....... *F02D 41/0027* (2013.01); *B60H 1/2206* (2013.01); *B60K 15/03006* (2013.01); *F02D 41/263* (2013.01); *G01N 33/225* (2013.01); *B60H 2001/224* (2013.01); *B60H 2001/2246* (2013.01); *B60H 2001/2284* (2013.01); *B60K 2015/03013* (2013.01); *B60K 2015/0321* (2013.01); *B60Y 2400/104* (2013.01); *F02D 2200/0611* (2013.01)

(58) Field of Classification Search
CPC ............... F02D 41/0027; F02D 41/263; F02D 2200/0611; F02D 41/405; F02D 2041/1411; F02D 2041/1433; B60H 1/2206; B60H 2001/224; B60H 2001/2284; B60H 2001/2246; B60K 15/03006; B60K 2015/03013; B60K 2015/0321; G01N 33/225; B60Y 2400/104
USPC ........ 123/1 A, 525, 480; 73/114.38; 701/106
See application file for complete search history.

(56) References Cited

U.S. PATENT DOCUMENTS

| | | | |
|---|---|---|---|
| 6,412,472 B1 * | 7/2002 | Tilagone | F02P 5/145 123/406.3 |
| 9,354,220 B2 * | 5/2016 | Rebinsky | F02D 41/3005 |

(Continued)

*Primary Examiner* — Hai Huynh
(74) *Attorney, Agent, or Firm* — Ivan M. Posey, Esq.; Leech Tishman Fuscaldo & Lampl, Inc.

(57) ABSTRACT

A system and method for configuring parameters for a variable gaseous appliance, comprise a sensor for detecting a composition of the gaseous fuel in a fuel tank. A first set of instructions are executable on a processor for receiving a signal from the sensor and analyzing the gaseous fuel based on the Wobbe Index, methane index, and inert gas percentage, to produce a gaseous fuel analysis. A second set of instructions are executable on the processor for producing a signal for configuring parameters of the engine for running the engine based on the gaseous fuel analysis.

28 Claims, 9 Drawing Sheets

(56) References Cited

U.S. PATENT DOCUMENTS

| | | | | |
|---|---|---|---|---|
| 2004/0195531 A1* | 10/2004 | Rahmouni | ............ | G01N 33/225 250/573 |
| 2009/0013759 A1* | 1/2009 | Knobloch | .............. | G01N 27/16 73/25.05 |
| 2010/0205976 A1* | 8/2010 | Nag | .......................... | F02C 9/40 60/775 |
| 2014/0326049 A1* | 11/2014 | Zelepouga | ............ | G01N 33/225 73/31.06 |
| 2017/0218837 A1* | 8/2017 | Zhong | .................... | F02B 37/183 |

* cited by examiner

FUEL SENSOR FOR A VARIABLE-BLEND NATURAL GAS APPLIANCE USING THE WOBBE INDEX

CROSS-REFERENCE TO RELATED APPLICATIONS

This application claims the benefit of U.S. Provisional Patent Application No. 62/239,808, titled "Online Wobbe Sensor for the Natural Gas by Indirect Measurement With Chemo-Metric Data," filed Oct. 9, 2015, the contents of which are incorporated herein by reference in their entirety.

FIELD OF THE INVENTION

The invention relates to an online fuel sensor technology for a variable-blend natural gas vehicle. Specifically, the online fuel sensor may be used in natural gas vehicles (NGVs), heating, ventilation and air conditioning (HVAC) systems, gas ranges, and the like, to provide them with the ability to accept a broader range of fuel using the Wobbe Index.

BACKGROUND OF THE PRIOR ART

Renewable Natural Gas (RNG) can be produced from carbonaceous and renewable feedstocks through a number of technologies including anaerobic digestion, landfill waste decomposition, gasification and pyrolysis. However, RNG contains a wide range of $CO_2$ depending on the source, production method, has to be upgraded by removing most of the $CO_2$ in order to meet the existing fuel specification of the Natural Gas Vehicle (NGV).

Further, NGVs typically operate with stoichiometric air-to-fuel ratio control with a three way catalyst (TWC) to control the emissions of NOx. One method for reducing NOx emissions further is with exhaust gas recirculation (EGR). EGR is the process of recirculating some of the exhaust with fresh air and fuel to minimize the nitrogen forming species. RNG has high levels of $CO_2$ which could provide the same NOx emissions reduction benefit of EGR, but without the EGR technology. This has two benefits, 1) the EGR system is not needed thus reducing engine costs and 2) complete separation is not needed, thus reduction the RNG production costs.

Therefore, a need exists for equipment and methods to ease the transition from conventional fossil based fuels to the widespread adoption of renewable nature gaseous (NGR) fuels, while reducing or eliminating the need for EGR technology. The present invention satisfies those needs, as well as others, and overcomes the deficiencies of previously developed vehicle and natural gas energy solutions.

SUMMARY OF THE INVENTION

According to one aspect of a preferred embodiment, a method for configuring parameters for a gas appliance for variable gaseous fuels, comprises: detecting a composition of the gaseous fuel using a sensor; receiving a signal from the sensor; analyzing the gaseous fuel based on one or more values of interest, the values of interest including Wobbe Index, methane index, and inert gas percentage, to produce an gaseous fuel analysis; and producing a signal for configuring parameters of the engine for running the engine based on the gaseous fuel analysis.

According to another aspect of a preferred embodiment, system for configuring parameters for a variable gaseous appliance, comprises: a sensor for detecting a composition of the gaseous fuel; a processor; a first set of instructions executable on the processor for receiving a signal from the sensor and analyzing the gaseous fuel based on the Wobbe Index, methane index, and inert gas percentage, to produce an gaseous fuel analysis; and a second set of instructions executable on the processor for producing a signal for configuring parameters of the gas appliance for running the engine based on the gaseous fuel analysis.

BRIEF DESCRIPTION OF THE DRAWINGS

These and other features, aspects and advantages of the present invention will become better understood with regard to the following description, appended claims, and accompanying figures where:

DETAILED DESCRIPTION OF THE PREFERRED EMBODIMENTS

Figure 1:
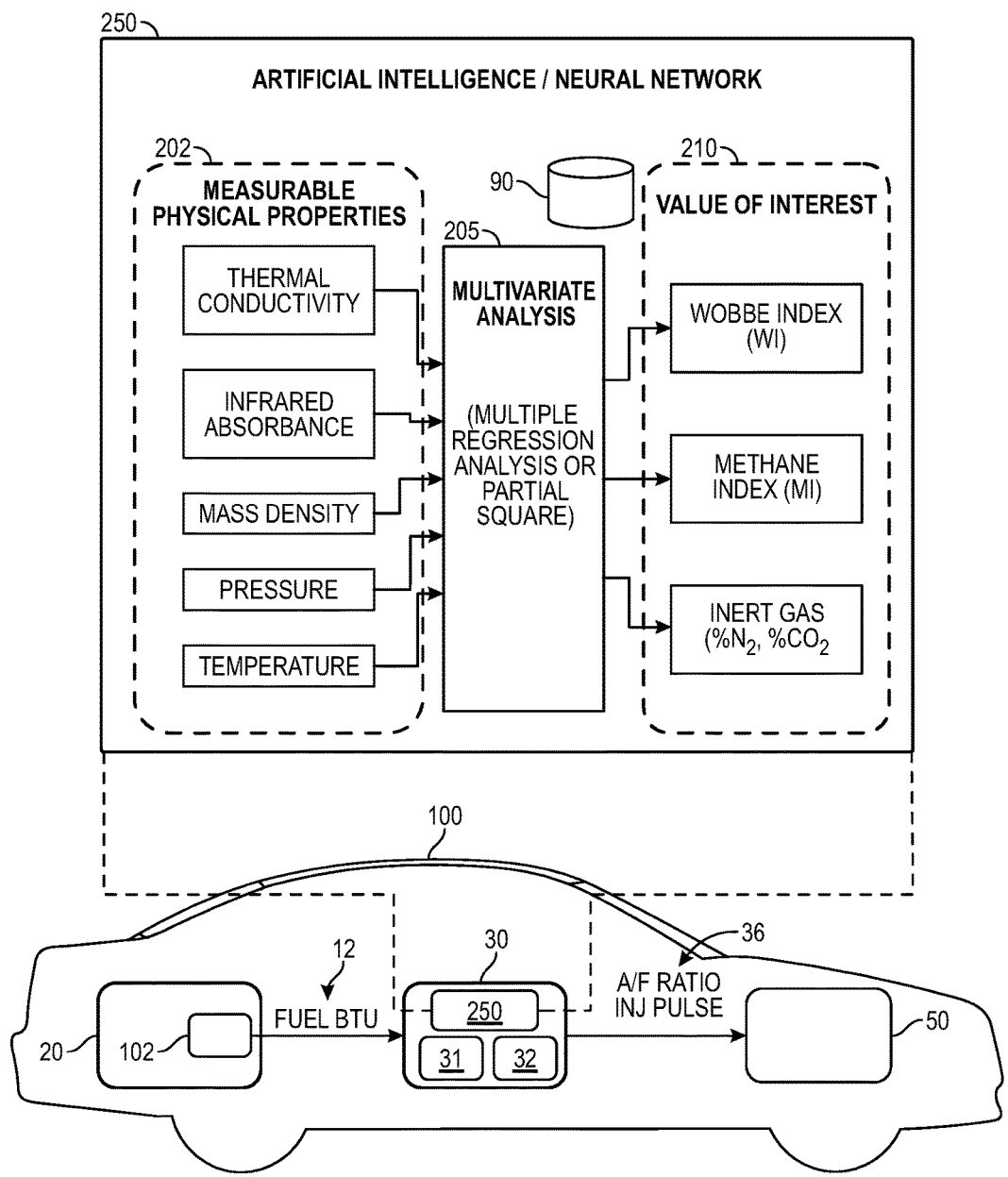
FIG. 1 is a high level schematic diagram that illustrates variable natural gas vehicle (VNGV) with an artificial intelligence module according to one embodiment.

For illustrative purposes, the present invention is embodied in the apparatus and method generally shown and described herein with reference to FIG. 1 through FIG. 11. It will be appreciated that the apparatus may vary as to configuration and as to details of the parts, and that the method may vary as to the specific steps and sequence, without departing from the basic concepts as disclosed herein.

Introduction

Renewable Natural Gas (RNG) is an important alternative fuel that can contribute to achieving a number of goals set by local and national governments related to conventional fuel replacement and Greenhouse Gas (GHG) emissions reduction in the transportation sector. Natural gas vehicles (NGVs) have achieved reasonable market penetration over the past decade. However, significant increase in the number of NGVs running on RNG is needed in order to make an impact on net GHG emissions. Most RNG projects are small to medium scale by nature and comprehensive gas cleanup/upgrading to meet NGV fuel specifications is often not feasible from a project economics perspective. This results in most RNG resources being left undeveloped or wasted, such as in the case of landfill gas flaring. Developing NGVs that are capable of accepting a broader range of RNG fuel properties can help achieve widespread RNG usage for transportation. The typical calorific value of RNG from biogas or landfill gas projects is around 50-60% of equal volume fossil Natural Gas (NG). Table 1 (from A. J. Bruijstens et al. "Biogas composition and engine performance, including database and biogas property model" Stockholm: Biogasmax (2008)) shows the composition of RNG from the various source along with conventional NG.

TABLE 1

Characteristics of different high methane fuels

| Type of fuel | Biogas | Natural Gas (fossil) |
|---|---|---|
| $CH_4$ | 50-75% | 97% $CH_4$ |
| $CO_2$ | 25-50% | — |
| $N_2$ | 0-10% | 0.4% |
| $H_2$ | 0-1% | — |
| $H_2S$ | 0-3% | — |
| $O_2$ | 0-0.5% | — |
| $C_2+$ | — | 2.6% |
| Wobbe Index ($MJ/m^3$) | 25-45 | ~50 |

A rugged, cost effective sensor produces signals that are interpreted using chemo-metric methods. The signals from the sensor are indexed and the Wobbe Index is indirectly determined in real time. In one embodiment, the accuracy of the sensor, based on the performance on other automotive sensors (ex., oxygen sensor), is at least within ±5% of the actual Wobbe Indices.

The Wobbe Index may be a critical factor in evaluating the interchangeability between different high methane fuels, and the present invention uses a Wobbe Index sensor for use in NGVs. In one embodiment, invention uses a combination of a thermal conductivity and an infrared sensor together with temperature and pressure measurement. The signals from these sensors are indexed in a method that estimates the Wobbe Index in real time. For example, in one embodiment of the sensor was confirmed to operate over a temperature range of −20° C. to 70° C. under pressures of up to ~3600 psi. A multivariate method estimates the fuel Wobbe Index from the measured temperature, pressure and thermal conductivity data.

The accuracy was improved to ±1% using the $CH_4$ concentration data from the infrared (IR) sensor additionally. Compared to the existing methods, this sensor provides a cost-effective, ruggedized solution that can be used in a variable-blend natural gas vehicle (VNGV), allowing refueling from a broad range of natural gas sources. This new sensor may to significantly increase RNG usage for transportation purposes.

Commercially available Wobbe Index measurement techniques typically involve bulky, complex and expensive analyzers. These devices measure the energy content of the fuel through direct combustion (calorimetry) and separately measure fuel density using optical methods. Past efforts to develop a portable Wobbe Index analyzer have also relied on direct calorific value measurement in a catalytic combustion chamber followed by sample density measurement. Such analyzers would be difficult to use in some embodiments, because they are bulky, and provide for a slow analysis. In addition, there may be safety concerns with using calorimetric analysis and there may be reliability issues in the harsh automotive environment.

System Architecture

The sensor provides the measurement of a multiple set of indirect variables to find the relationships between the indirect variables and the Wobbe Index. The higher number of independent variables, which provide different responses to the fuel composition changes, results the better prediction. In addition to the pressure and temperature measurement of the fuel, thermal methane fuels. A key enabling technology required to develop VNGVs is an on-line fuel Wobbe Index sensor that can measure the fuel's index in real time.

With reference to FIG. 1, a high level schematic diagram illustrating a variable natural gas vehicle (VNGV) 100 according to one embodiment with a built-in fuel Wobbe Index sensor 10 is shown in FIG. 1. In one embodiment The Wobbe Index sensor 10 is located in the fuel tank 20, or in the fuel line, and directly communicates with the engine control unit (ECU) 30. A first set instructions 31 that are executable on the ECU 30 in the engine control software or firmware enables the ECU 30 to read signals 12 produced by the sensor 10. A second set of instructions 32 executable on the ECU 30 may then determine an adjustment that can be made to the fuel injector pulse width of the engine 50, so that a signal 36 may be sent to the engine 50 to adjust the fuel injector pulse width according to an index database 90 created using the Wobbe Index, Methane Index, and inert gas composition using an artificial intelligence system 250.

In one embodiment, the second set of instructions 32 may include, in the signal 36 sent to, the engine parameters for adjusting the ignition timing of the engine 50 based on the $CH_4$ content.

FIG. 1 illustrates the flow of data and analysis 200 that goes into the index database 90. In FIG. 1, the diagram is in the context of natural gas vehicles (NGVs) 100. However, those of skill in the art would recognize that the system may be applied to any systems that run on natural gas, for example, HVACs and gas appliances, and the like. In the context of FIG. 1, NGVs typically operate with stoichiometric air-to-fuel ratio control with a three way catalyst (TWC) to control the emissions of NOx. One method for reducing NOx emissions further is with exhaust gas recirculation (EGR). EGR is the process of recirculating some of the exhaust with fresh air and fuel to minimize the Nitrogen forming species. RNG has high levels of $CO_2$ which could provide the same NOx emissions reduction benefit of EGR, but without the EGR technology. This has two benefits, 1) the EGR system is not needed thus reducing engine costs and 2) complete separation is not needed, thus reduction the RNG production costs.

The system and method herein provides a new operating mode for NGV engines, HVAC, and natural gas appliances, which can combust the unprocessed RNG (RNG with $CO_2$), where the EGR is process is removed or minimized.

Table 2 below shows the composition of typical RNG from two different sources along with conventional natural gas.

TABLE 2

Composition of typical RNG from two different sources along with conventional natural gas

| Types of RNG | Biogas 1 Household waste | Biogas 2 Agrifood industry | Natural gas |
|---|---|---|---|
| Composition | 60% CH4 | 68% CH4 | 97% CH4 |
|  | 33% CO2 | 26% CO2 | 2.2% C2 |
|  | 1% N2 | 1% N2 | 0.3% C3 |
|  | 0% O2 | 0% O2 | 0.1% C4+ |
|  | 6% H2O | 5% H2O | 0.4% N2 |
| Caloric Value kWh/m3 | 6.0 | 6.8 | 10.3 |
| Density | 0.93 | 0.85 | 0.57 |

TABLE 2-continued

Composition of typical RNG from two different sources along with conventional natural gas

| Types of RNG | Biogas 1 Household waste | Biogas 2 Agrifood industry | Natural gas |
|---|---|---|---|
| Mass (kg/m3) | 1.21 | 1.11 | 0.73 |
| Wobbe Number | 6.9 | 8.1 | 14.9 |

EGR equipped engines, for example, utilize between 0-25% of the exhaust flow. The 25% EGR matches well with RNG inert $CO_2$ composition which is in between 26% to 33% (see table above). Fossil based NG has no measurable $CO_2$. (See Table 2 above).

With reference back to FIG. 1, an artificial intelligence system or neural network module 250 may be included, wherein the artificial intelligence module includes tools 205, such as multivariate analysis algorithms, multiple regression analysis, and/or partial least square models. The analysis tools may take, as input data, Measurable Physical Properties 202, such as thermal conductivity, infrared absorbance, mass density, pressure, and temperature. These Measurable Physical Properties 202 are fed into the analysis tools 205, to produce estimates of fuel properties, which are called "Values of Interest" 210, which may include stored values for each of different fuel compositions that can be determined by the Wobbe Index (WI), methane (MI), and percentage of inert gases (% Inert). More detail regarding the creation of the database 90 that may be updated by the sensor 102 and access within artificial intelligence system 250 is provided below.

In one embodiment, the sensor 102 may measure of a multiple set of indirect variables to find the relationships between the indirect variables and the Wobbe Index, Methane Index, and inert gas composition. The higher number of independent variables, which provide different responses to the fuel composition changes, results, the better the prediction. In addition to the pressure and temperature measurement of the fuel, thermal conductivity and/or point infrared sensors were selected as candidate technologies, since these measurements are proven reliability in the temperature range of −20° C. to 50° C. and pressures of up to 3600 psi, which is the common specification as the automotive application. Table 3 summarizes the characteristics of two types of sensors: thermal conductivity detectors, and point infrared detectors.

TABLE 3

Characteristics of candidate sensors.

| Gas sensor type | Benefits | Issues |
|---|---|---|
| Thermal Conductivity | Can measures concentrations of gas mixtures even in the absence of oxygen. | High gas concentration only. Limited range of gases. Fragile (wire type). |
| Point Infrared | Selective measurement to the certain species. Can be used in inert atmospheres. Can be located inside the fuel tank/fuel line | Low sensitivity. Higher cost than Thermal Conductivity. Sensor with the gas cell cannot be used because of pressure rating |

Thermal Conductivity Detectors

A thermal conductivity detector (TCD) measures the thermal conductivities of the gas. This detector contains a sensing element (typically filament or film) that is heated electrically so that it is hotter than the surrounding gas. The temperature difference between the surrounding gas and sensor is directly related to thermal conductivity of the gas.

Since the thermal conductivity of $CH_4$ is almost twice as high as that of $CO_2$, it can be used as the major indexing signal that distinguishes RNG from conventional NG. TCDs can operate over a wide range of temperatures and pressures. The operating temperature and pressure range of a typical TCD covers and exceeds the required parameter range for the use as the sensor 10.

The major advantages of TCD for the current application as the VNGV sensor 10 are:

Hot film anemometer, a technology similar to TCD, is widely used as mass air flow sensor in automotive applications, proving the cost-effectiveness, ruggedness, and reliability of the TCD technology.

Routine calibration is not required and the sensor is virtually maintenance free.

It can operate in continuous presence of gases in pressurized environments, and covers wide temperature ranges.

It has a universal response to the all gas species. This characteristic, when combined with a specific detector such as the infrared sensor, provides an excellent chemo-metric analysis option.

The only concern with using a TCD-type sensor is that it may be prone to surface oxidation due to residual oxidative impurities such as trace oxygen in the fuel mix. However, this concern can be reduced by using tungsten-rhenium as the sensing material, since it provides a chemically passivated layer on the sensing element.

Infrared Detectors

Infrared (IR) absorption technology based gas analysis has been used successfully for decades. Similar to TCDs, there is no chemical reaction between the gas and the sensor element in IR sensors. They are less susceptible to long-term drift and unlike chemical sensors, are resistant to contamination. Because of these properties, IR absorption sensors can operate over a wide range of temperatures as long as the sensor material is chemically and physically stable throughout the operating temperature range. The typical operating temperature range of −20° C. to 70° C. meets target temperature range required for the current application.

Infrared gas detection is based upon the ability of some gases to absorb IR radiation. Most hydrocarbons, including methane, absorb IR radiation at approximately 3.4 mm in wavelength whereas $H_2O$ and $CO_2$ are relatively transparent in this region. Therefore, a dedicated configuration operating at this wavelength can be used to detect $CH_4$.

The major advantages of IR gas detectors 9 for the current application are:

Immunity to contamination and poisoning.

Routine calibration is not required and the sensor is virtually maintenance free.

Ability to operate in the absence of oxygen or air.

Can operate in continuous presence of gases in pressurized environments.

Can be calibrated to response to specific species such as $CH_4$. This characteristics, when combined with a non-specific detector such as TCD, provides an excellent chemo-metric analysis option.

The drawback is that the IR sensors may have a high initial cost. IR sensors 9 have in the past been more expensive than other types of sensors, but their price is rapidly decreasing.

A commercially available point type infrared gas sensor from the Dynament Ltd, UK, may be used and was selected for testing. The maximum operating pressure of an IR absorption sensor is determined by the sealing or encapsulating techniques used to integrate the sensor to the fuel tank or fuel line. The pressure rating of the infrared window of the sensor element does not influence the maximum operating pressure since the inside of the window is pressurized by the same environment as the outside during operation. In testing, the sensors are located inside the fuel tank, and sealing was performed by blazing followed by thermal compression with high pressure electrical feed-thru. This type of sealing can easily withstand the proposed maximum operating pressure of 3600 psi.

Tested Installation

A sensor testing setup, including a manifold, was tested with a miniature stainless steel gas tank. The entire setup was located within a temperature controlled chamber. Characteristics of the components used in this setup are summarized in Table 4.

TABLE 4

Specification of sensors and components used in this study.

| Part Name | Part Number | Vendor | Specs |
| --- | --- | --- | --- |
| Double-Ended Cylinder | 316L-HDF4-300 | Swagelok | 316L SS Double-Ended DOT-Compliant Sample Cylinder, 1/4 in. FNPT, 300 cm3, 4000 psig. |
| Thermal Conductivity Sensor | N/A | In-House (by Bourns Inc.) | TCD, TUNGSTEN-RHENIUM Film and Filament (Copper seal) on Alumina Substrate |
| Premier Dual Gas IR SENSOR FOR HCs and CO2 | MSH-DP/HC/CO2/P | Dynament Inc. | Methane from 0 to 100% volume with 0.1% volume resolution, 0-2% volume propane, 0-5% CO2 with 0.01% resolution. |

Figure 2A:
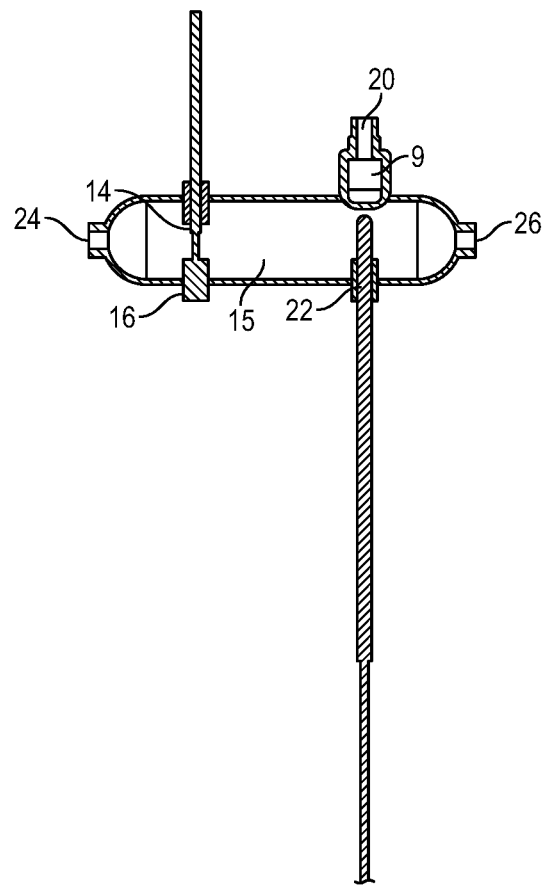
FIG. 2A is a diagrammatic illustration of a sensor according to one embodiment.

With reference to FIG. 2A, a diagrammatic illustration of the sensor 102 according to one embodiment is shown. A thermal conductivity (TC) Filament 14 from SRI Instruments, Inc. of Torrance, Calif. was used through a with a plug 16. An infrared (IR) sensor 102 from Dynament, Ltd. (sold as the Premier dual gas IR sensor) of the United Kingdom was utilized with a bell adapter 20. A thermocouple 22 may measure temperature. On either side of the sensor 102 is an inlet 24 and exhaust 26.

Figure 2B:
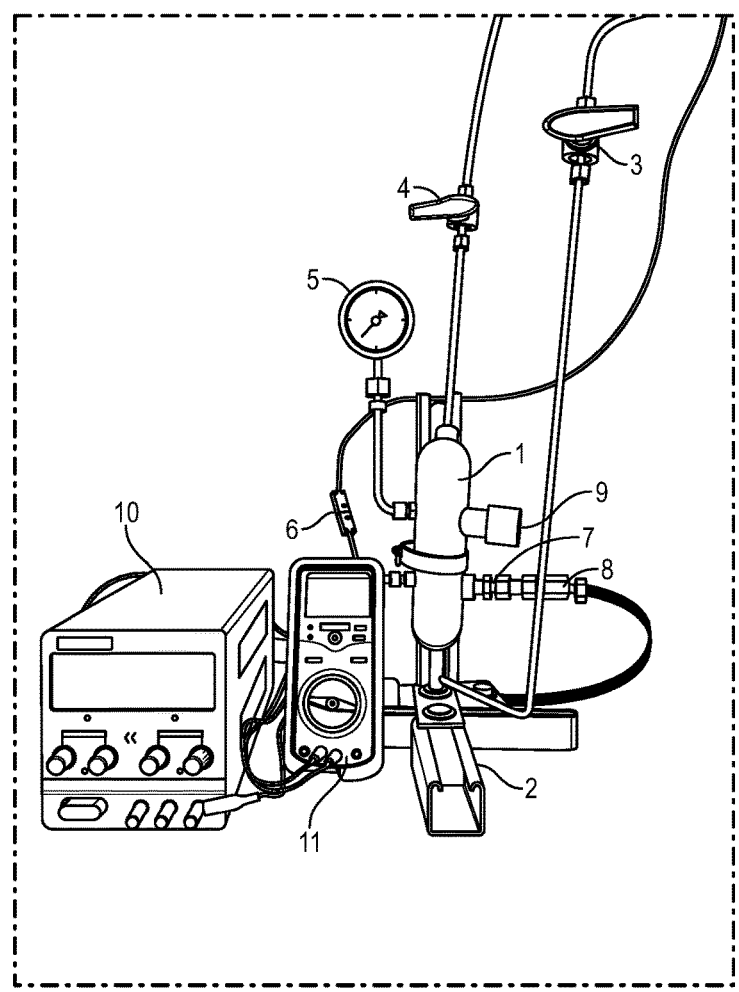
FIG. 2B is a diagrammatic illustration of a sensor that was used for testing according to another embodiment.

With reference to FIG. 2B, a diagrammatic representation of a test embodiment that was built is shown. In one embodiment, the sensor comprises a high-pressure stainless steel vessel 1 that is rated for a pressure of 4000 psi. The vessel may 1/4" female NPT fittings at the top and bottom. A Frame 2 may be used to hold vessel upright. A 1/4" ball valve 3 may be used to control the gas inlet. A. 1/4" ball valve 4 may be used to control the gas outlet. A pressure gauge 5 may be used to measure the pressure. A thermocouple 6 may be used to measure the temperature. A Rhenium-Tungsten material also known as a thermal conductivity detector (TCD) 7 may also be included. A high pressure feed-thru 8 and a Dynamite IR sensor 9 may also be included. A DC power supply 10 may be used to provide a constant current to the thermal conductivity sensor.

Figure 3:
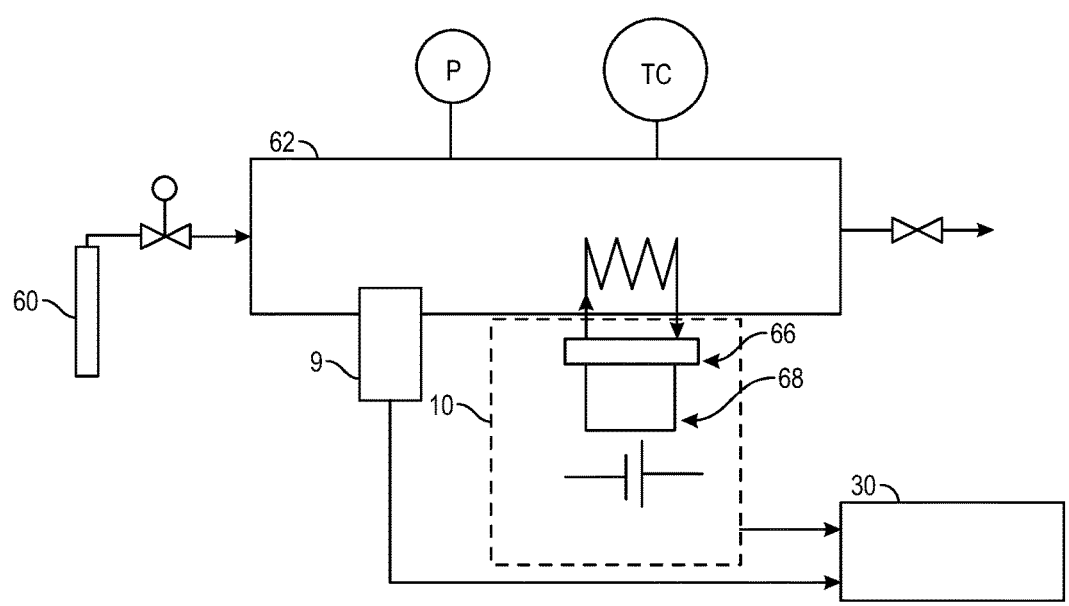
FIG. 3 is a schematic diagram of the test setup according to one embodiment.

With reference to FIG. 3, a schematic diagram of the test setup is shown. A gas cylinder 60 feeds into a sensor housing 62, which houses an IR sensor 9. The IR sensor 9 is electrically connected to an ECU 30 or computer 64 which receives measurement signals. A Rhenium-tungsten filament 66 and a high pressure feed-thru 68 was utilized, as was a direct current (DC) power supply 10. The ECU 30, or computer in the case of a test setup, is in electrical communication with the IR sensor 9.

Sensor Signal Interpretation to Wobbe Index

Parameters including fuel temperature, fuel pressure, TCD sensor output and IR sensor output were measured during testing. For the Thermal conductivity value, resistance of the TCD sensor at varying current that flows to the sensor was measured using a 4-probe digital ohm meter with constant current source (HIOKI PS100). The resistance of the TCD at zero current was measured and used to calculate the temperature of the gas since the resistance of the filament is directly proportional to the temperature of the surrounding gas under given conditions.

The Wobbe Indices of four different gas mixtures were measured during the experiments:
1. Industrial grade methane which has a purity of 99.99%.
2. A mixture of 95% $CH_4$, 4% ethane and 1% $CO_2$, which represents fossil NG.
3. A mixture of 60% $CH_4$, 39% $CO_2$, and 1% $N_2$, which represents RNG from household waste.
4. A mixture of 80% $CH_4$, 18% $CO_2$, 1% $O_2$, 1% $N_2$, which represents a median between the NG and RNG.

These are reported in the literature. All of the mixture gas was obtained as calibration gas grade bottle, traceable to the ASTM standard gas, which enables the providing of the actual Wobble Index from the ASPEN HYSYS fluid property model.

The relationship between temperature and resistance can be expressed as a simplified Callendar-Van Dusen equation:

$$R_T = R_0(1 + \alpha \times T) \quad \text{(Equation 1)}$$

Where:
$R_T$=Resistance it temperature T ($\Omega$)
$R_0$=Resistance at T=0° C. ($\Omega$)
$\alpha$=Temperature coefficient T=0° C. ($\Omega/\Omega/°$ C.)
$R_0$ and $\alpha$ values were measured to 30.19±0.11$\Omega$ and (32.4±0.23)×$10^{-4}$ $\Omega/\Omega/°$ C. respectively with a 95% confidence level. From the equation, the gas temperature was calculated with a ±1° C. accuracy without use of any additional temperature sensors. A commercially available pressure transducer (Omega Inc.) was used to measure the fuel pressure. The IR sensor 9 was calibrated for all anticipated $CH_4$ concentrations.

The Wobbe Index of the mixture gas was estimated using a four dimensional curve fitting algorithm. The Multiple Linear Regression method was derived using the multi variate analysis (MVA) function of MATLAB, which is a commercially available data analysis software package from The MathWorks, Inc. of Natick, Mass., United States.

The Wobbe Index, WI, can be derived as follows.

$$WI = f(P, T, E1, E2) \quad \text{(Equation 2)}$$

Where:
f(P, T, E1, E2)=4 dimensional curve fitting equation
T=Temperature
P=Pressure
E1=TCD sensor signal
E2=IR sensor signal The Wobbe Indices of the gas mixtures were also calculated using the Aspen HYSYS10 fluid property model with the Non-Random-Two-Liquid (NRTL) equation as the basis for calculations. Since this calculation is based on the known gas composition of calibration gas, it provides the verification of the accuracy of proposed measurement. The calculated Wobbe Indices were found to be in the same range as the values reported in literature.

Test Results

Figure 4:
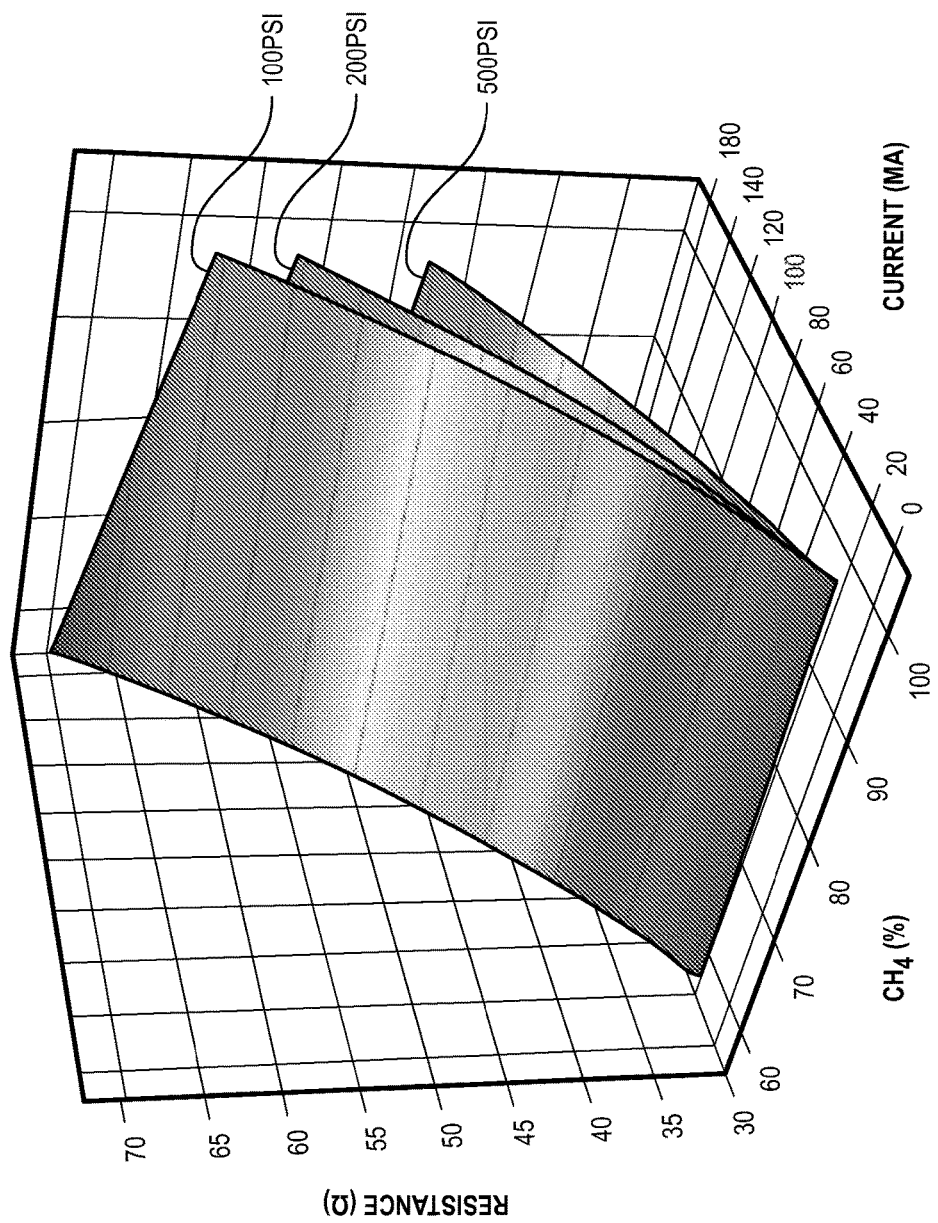
FIG. 4 is a graph that shows the resistance of different gas mixtures against the supplied current values under different pressures according to one embodiment.

FIG. 4 shows the resistance (Z axis, in ohm) of the different gas mixtures (X axis, in percentage $CH_4$) against the supplied current values (Y axis, in mA) under different pressures. For convenience, thermal conductivity of the gas was measured as the filament resistance of the TCD sensor, since the thermal conductivity is reversely proportional to the surface temperature of the filament in the TCD sensor. The surface temperature of the sensor is a linear function of sensor (filament) resistance, as shown by the Callendar-Van Dusen equation (1).

The plot shows that as the pressure increases, the measured resistance drops, implying reduced sensitivity (slope of the Resistance vs Current curve) in the resistance measurement. This behavior is expected, since under higher pressures, higher population of the gas molecules, which act as a heat carrier, lead to reduced sensitivity, (i.e. less difference in resistance among different gases). Based on this behavior, it is recommended that the sensor be located in the place with lower fuel pressure, such as downstream of fuel pressure regulator, instead of directly locating inside of the fuel tank.

Figure 5:
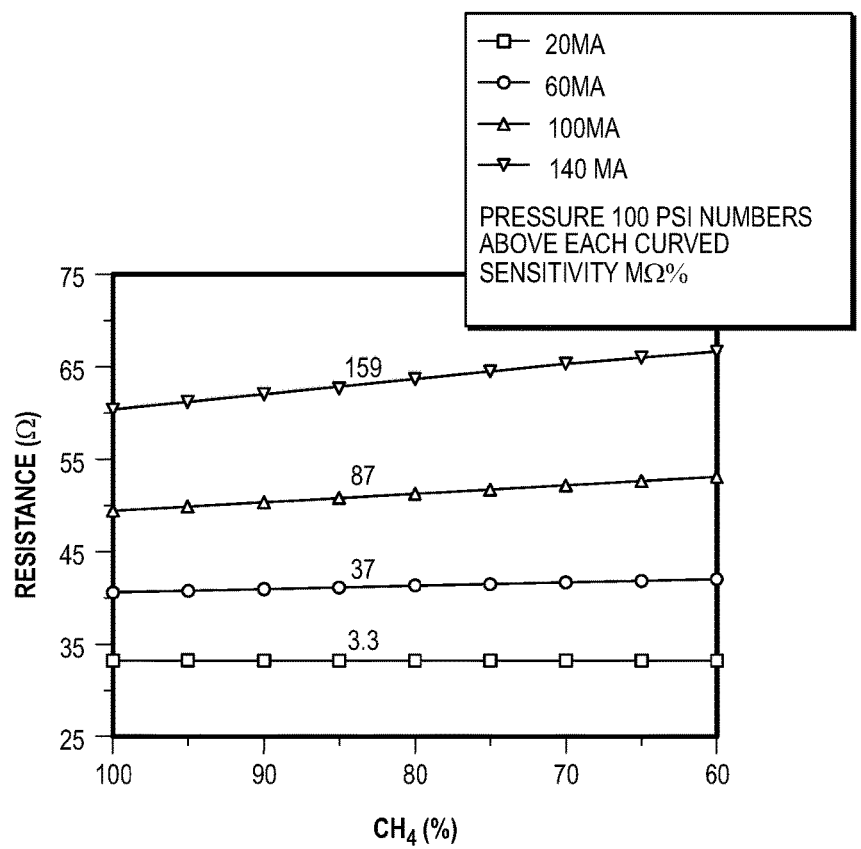
FIG. 5 is a graph that shows the relationship of TCD resistance to the gas composition.

It should be noted that there is no measurable difference than 1% in the resistance of the gas mixtures until the TCD excitation current is increased to around 50 mA. This is true for all the different pressures. FIG. 5 shows that at higher TCD excitation currents, the slope of curve increases. A value of 100 mA was chosen as the excitation current for further tests. This value is the median between the 50 mA minimum and the manufacturer's recommended maximum continuous current of 150 mA. This value provides a sensitivity of 87 (slope of the curve, change of the resistance per unit concentration change, $\Delta m\Omega/\Delta\%$), which is large enough sensitivity for the resistance measuring device with $0.1\Omega$ resolution.

Figure 6:
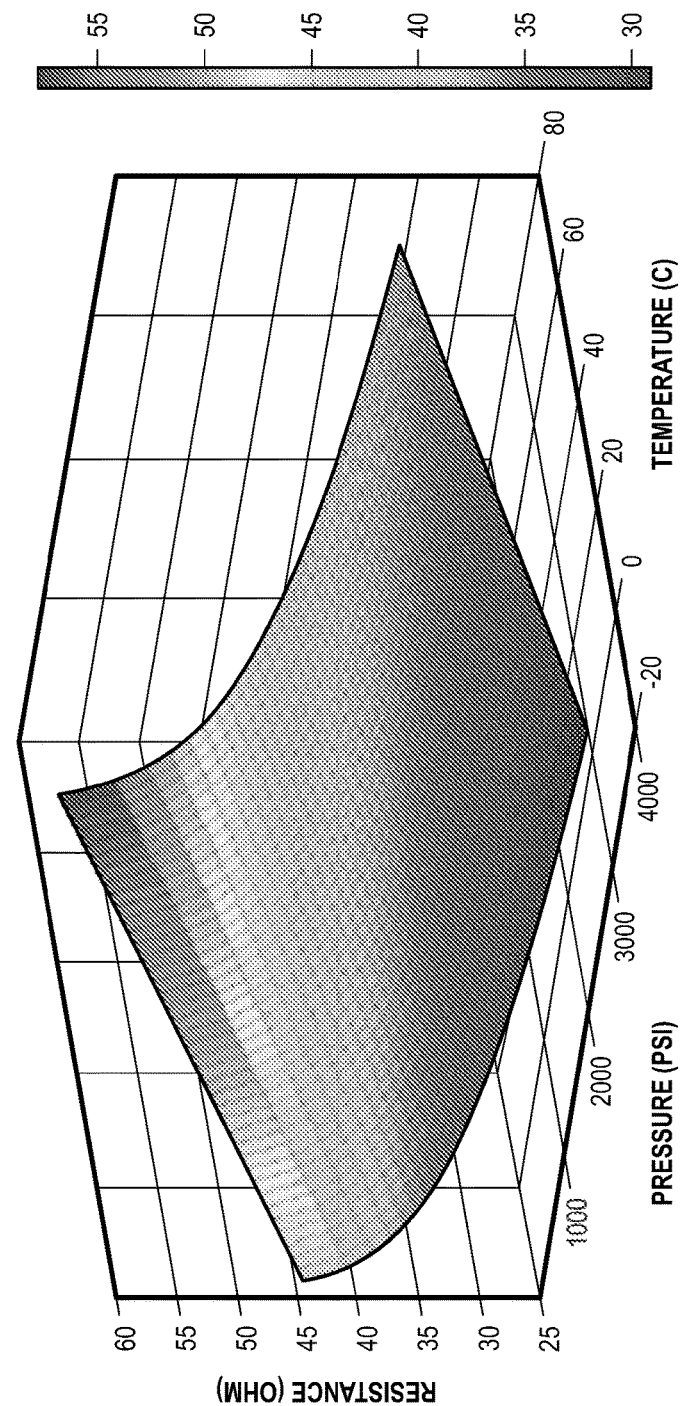
FIG. 6 is a graph that shows the relationship of TCD resistance to the Wobbe Index at 25° C. and 500 psi.

FIG. 6 shows the TCD resistance map for the entire temperature (−20° C.-70° C.) and pressure range (~3600 psi) at 100 mA of TCD excitation current. As the pressure increases the resistance decreases exponentially and plateaus around the value of surrounding temperature, i.e. the value from the Callendar-Van Dusen equation (1), which is the resistance of the sensor when zero current is supplied. As discussed earlier, the effect of temperature on resistance is in the form of a linear relationship.

Figure 7:
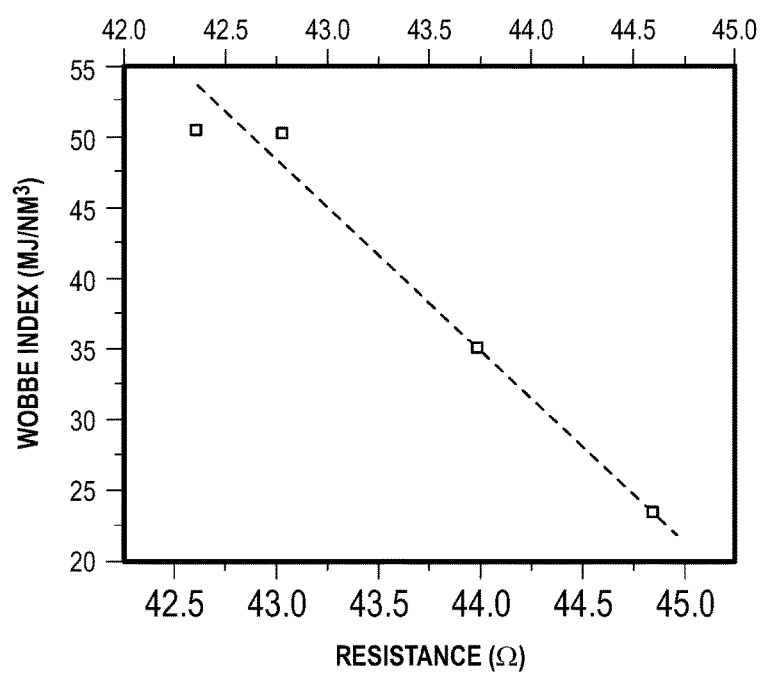
FIG. 7 is a graph that shows a dotted line which represents the optimum equation to predict the Wobbe Index from the measurement of TCD resistance, pressure and temperature shown in FIG. 6.

FIG. 7 shows the dotted line which represents the optimum equation to predict the Wobbe Index from the measurement of TCD resistance, pressure and temperature shown in FIG. 6. This regression line, obtained using multiple linear regression analysis in the MATLAB tool box, shows the predicted Wobble Index value. The equation can be formulated as:

$$Y = (0.0102 \times P^{2.105} \times T - 3.701 \times P^{2.155}) \times R + 347.85 \times P^{0.90} \quad \text{(Equation 3)}$$

Where:
Y is the Wobbe Index (MJ/Nm^3),
P is the pressure in psi,
T is the temperature in Celsius, and
R is the TCD resistance in ohms.

Real Wobbe Index values obtained from the ASPEN analysis from the gas composition for the 4 set of the gas mixture are also shown as square dot in FIG. 7. The deviation from the ASPEN value to the predicted value from the above equation was maximum 5% throughout the entire temperature and pressure range.

Estimation of the Wobbe Index by the TCD sensor rely on the fact that $CH_4$ has the highest thermal conductivity among the components present in the gas mixtures and it constitutes the major component in the natural gas. However, with reference back to the process 200 in FIG. 1, other gas species also contribute the thermal conductivity of the gas mixture. The accuracy of the estimated Wobbe Index was significantly increased by constraining the regression further using the data from the IR sensor 9 since the IR sensor 9 provides an independent measurement of $CH_4$ concentration in the gas mixture. Another important parameter for NG engines, the "Methane Index" can be measured as well since IR sensor 9 provides a direct measurement of CH4 over the entire temperature and pressure range. By adding the $CH_4$ measurement data in the algorithm, the accuracy was improved up to 1%. This is mainly because total number of independent variable is increased to 4 from 3. (TCD, IR sensor, pressure and temperature), which enables to develop more precise algorithm or regression fit. The optimum implementation algorithm, given in equation (4), uses a weighted average to obtain the corrected Wobbe index. The weighted average was taken between the Wobbe Index from equation (3) and the Wobbe Index as it relates to the CH4% from infrared sensor 9.

The corrected Wobbe Index is:

$$W = \frac{X}{100} * C + \frac{100 - X}{100} * Y \quad \text{(Equation 4)}$$

Where:
W is the corrected Wobbe Index (MJ/Nm^3),
X is the signal from IR sensor in methane mode in $CH_4$%
C is a correction coefficient summarized in below.
If the X is in the range of 100-90, C=50
If the X is in the range of 89-70, C=35
If the X is in the range of 69-50, C=20
Y is the Wobbe Index from the equation (3).

To summarize, a Wobbe Index sensor for use in NGVs was designed and successfully calibrated using four different gas mixtures. The system uses a combination of a TCD and an IR sensor 9 and the signals from the sensor are indexed in an algorithm that estimates the Wobbe Index in real time. This system is a major step towards significantly increasing RNG use in transportation sector. The sensor 102 was confirmed to operate over at least a temperature range of −20° C. to 70° C. under pressures of at least up to ~3600 psi. The AI 250 may include a multivariate algorithm (205 in FIG. 1) that is used to estimate the fuel Wobbe Index value with a ±5% accuracy from the measured temperature, pressure, mass density, infrared absorbance and thermal conductivity data of the Measurable Physical Properties (202 in AI 250 in FIG. 1). The accuracy was further improved to ±1% using the $CH_4$ concentration data from IR sensor 9 additionally.

The VNGV engine system of FIG. 1 incorporates the Wobbe Index sensor 102, modified engine control unit (ECU) 30 with the multivariate algorithm and NG engine. The system is able to alter the injector pulse width in response to the fuel Wobbe Index. An additional feature is the ability to alter the ignition timing based on the fuel $CH_4$ content (methane index).

The AI module 250 may use the sensor 102 to estimate the fuel property, which is called a "Value of Interest" (WI, MI, and % Inert) in the AI learning model or neural network. Based on the Value of Interest model 210 created by the artificial intelligence/neural network (AI) system 250 of FIG. 1, a sensor system may provide for on-board detection of fuel properties for VNGV 100, HVACS, and gas appliances. With reference back to FIG. 1, The relationships established in the AI system 250 between Measurable Physical Properties 202 collected from sensors and the Value of Interest 210 comprises the AI learning model. This method is desirable due to the difficulties in directly measuring the Value of Interest 210 by the sensor 102 itself, while the Measurable Physical Properties 202 of a fuel (such as thermal conductivity, infrared absorbance, mass density, pressure or temperature) can be easily obtained.

Further, in one embodiment, the ECU itself include the AI system 250 itself to store and use data on new fuel mixtures that may be found from time to time. In one embodiment, the ECU 30 may collect data from both the sensor 102 and the AI system 250 in the analysis to create control signals 36 to the engine 50, HVAC or appliance.

Figure 8A:
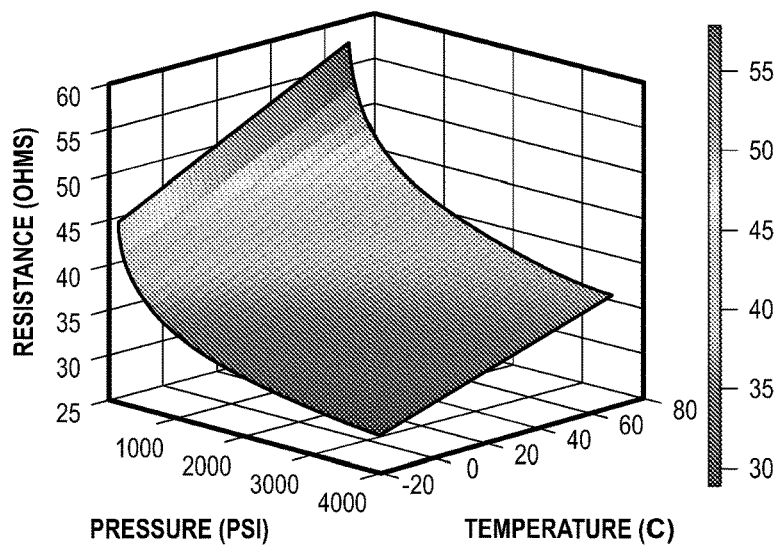
FIG. 8A is a first graph illustrating data that may be used to estimate the Wobbe Index.
Figure 8B:
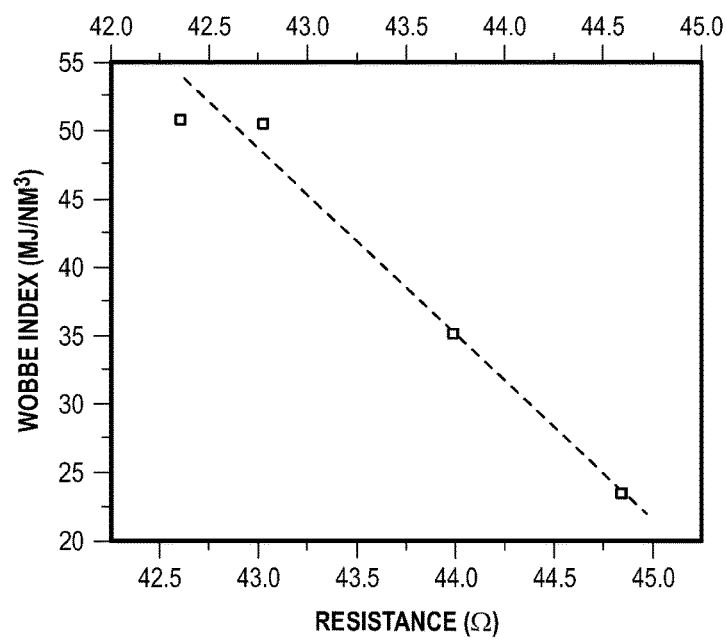
FIG. 8B is a that graph illustrating data that may be used to estimate the Wobbe Index.

The AI system 250 may use the thermal conductivity data of the Measurable physical Properties to estimate the WI within 5% accuracy using a simple regression method 205 as shown in FIGS. 8A and 8B. Here, the number of Value of Interest parameters 210 to be estimated is increased to three (WI, MI and % Inert) from one WI. In one embodiment, the system may use a more sophisticated statistical analysis approach such as the Multivariate Analysis (MVA) and a machine learning method in the Artificial Neural Network (ANN) 250 to build a more accurate model. MVA is a well-known statistical analysis method and ANN is a powerful machine learning approach in the Artificial Intelligence area. Both methods are powerful enough to create linear and nonlinear models. In addition, both methods can be also used to verify the accuracy of the model. Tools for building a model using both of these methods are available in chemo-metric software such as CAMO unscrambler or MATLAB Toolbox.

The number of "Measurable Physical Property" parameters 202 is also increased in the one embodiment. Sonic orifice in the fuel line may be used to estimate the mass density along with the molar density of the gas by measuring pressure, temperature and thermal conductivity of the fuel.

A target accuracy to achieve is +/−1% rel. and stability of +/−0.5% rel. for all three Values of Interest 210 leads to satisfactory engine performance during variable blended fuel operation in an engine 50. Optimum combustion phasing may be ensured so there is no impact on brake specific energy consumption with feedback from the fuel sensor and closed loop combustion control. A system using multivariate analysis and ANN allows creation of an accurate model that estimates the three Values of Interest 210 from fuel properties collected from the sensor 102 and develop an accurate on-board fuel property detection system. Risks of incorrect prediction of Value of Interest can be minimized by addition of commercially available engine/powertrain sensors such as intake and exhaust gas sensors or measuring infrared gas absorbance.

Database

With reference back to FIG. 1 a database 90 in the AI module 250 of blended fuel compositions may be constructed and used real time by the AI module 250 of the ECU 30. The ECU may also be wired or wireless connected for update from outside vendors by such technologies as 4G, 3G, LTE, WiFi, Wimax, or the like. Existing compositional information of biogas from landfill, anaerobic digesters and household waste may be collected together with those from fossil sources where appropriate.

Measurable Physical Properties 202 of each blended fuel mixture at varying pressures and temperatures may be estimated using CHEMKIN, a well-known software tool that can use compositional information to estimate transport properties of the gas mixture, including thermal conductivity, mass/mole density and infrared absorbance.

The Value of Interest (WI, MI) 210 for each case may be estimated using Aspen Plus simulation model from the known compositional information. Inert gas composition is directly collected without relying on simulation.

An MVA and ANN model 250 that describes the relationships between Measurable Physical Properties 202 and the Values of Interest 210 may use tools such as CAMO Unscrambler or MATLAB w/ Chemo-metric Toolbox. The most efficient and economical way of collecting Measurable Physical Properties 202 to achieve desired target performance can then be identified.

The various embodiments described above are provided by way of illustration only, and should not be construed to limit the invention. Those skilled in the art will readily recognize various modifications and changes that may be made to the claimed invention without following the example embodiments and applications illustrated and described herein, and without departing from the true spirit and scope of the claimed invention, which is set forth in the following claims.

What is claimed is:

1. A method for configuring parameters for a gas appliance for variable gaseous fuels, comprising:
   detecting a composition of the gaseous fuel using a sensor;
   receiving a signal from the sensor;
   analyzing the gaseous fuel based on one or more values of interest, the values of interest including Wobbe Index, methane index, and inert gas percentage, to produce a gaseous fuel analysis, wherein the step of analyzing is performed by a learning-artificial intelligence module; and
   producing a signal for configuring parameters of the gas appliance for running the gas appliance based on the gaseous fuel analysis.

2. The method of claim 1, wherein the gas appliance comprises an HVAC.

3. The method of claim 1, wherein the gas appliance comprises an automobile engine in an automobile.

4. The method of claim 3, wherein the values of interest are derived by an artificial intelligence module that is readable by an ECU in the automobile, the artificial intelligence module capable of deriving said values of interest from one or more measurable physical properties of gaseous fuel selected from the type consisting of: thermal conductivity, infrared absorbance, mass density, pressure, temperature and mole density.

5. The method of claim 1, wherein the sensor comprises an infrared detector.

6. The method of claim 1, wherein the sensor comprises a thermal conductivity detector.

7. The method of claim 1, wherein the sensor comprises a mole density detector.

8. The method of claim 1, wherein the gaseous fuel may comprise one or more mixtures of gaseous fuel having one or more BTU contents.

9. The method of claim 1, wherein the gaseous fuel analysis is based one or more RNG composition databases.

10. The method of claim 1, further comprising placing the sensor in a fuel tank of a vehicle.

11. The method of claim 1, further comprising placing the sensor in a chamber that is spliced in-line with a fuel line.

12. The method of claim 1, further comprising reading the values of interest from a database in real time to perform the analyzing of the gaseous fuel.

13. The method of claim 12, comprising updating measurable physical properties based on the composition of the gaseous fuel detected by the sensor.

14. The method of claim 13, analyzing and updating the values of interest in the database using an artificial intelligence module based on the step of updating the measurable physical properties.

15. A system for configuring parameters for a variable gas appliance, comprising:
   a sensor for detecting a composition of the gaseous fuel in a fuel tank;
   a processor that includes a learning artificial intelligence module;
   a first set of instructions executable on the processor for receiving a signal from the sensor and analyzing the gaseous fuel based on the Wobbe Index, methane index, and inert gas percentage, to produce a gaseous fuel analysis using the learning artificial intelligence module; and
   a second set of instructions executable on the processor for producing a signal for configuring parameters of the gas appliance for running the gas appliance based on the gaseous fuel analysis.

16. The system of claim 15, wherein the gas appliance comprises an HVAC.

17. The system of claim 15, wherein the gas appliance comprises an automobile engine in an automobile.

18. The system of claim 17, wherein one or more values of interest are derived by an artificial intelligence module in an ECU in the automobile, the artificial intelligence module capable of deriving said values of interest from one or more measurable physical properties of gaseous fuel selected from the type consisting of: thermal conductivity, infrared absorbance, mass density, pressure, temperature and mole density.

19. The system of claim 15, wherein the sensor comprises an infrared detector.

20. The system of claim 15, wherein the sensor comprises a thermal conductivity detector.

21. The system of claim 15, wherein the sensor comprises a mole density detector.

22. The system of claim 15, wherein the gaseous fuel comprises one or more mixtures of gaseous fuel having one or more BTU contents.

23. The system of claim 15, wherein the gaseous fuel analysis is based one or more RNG composition databases.

24. The system of claim 15, wherein the sensor is in a fuel tank of a vehicle.

25. The system of claim 15, wherein the sensor is in a chamber that is spliced in-line with a fuel line.

26. The system of claim 15, wherein the values of interest are stored in a database capable of being read in real time to perform the analyzing of the gaseous fuel.

27. The system of claim 26, wherein one or more measurable physical properties are capable of being updated based on the composition of the gaseous fuel detected by the sensor.

28. The system of claim 27, wherein an artificial intelligence module is capable of analyzing and updating one or more values of interest in the database based on the measurable physical properties.

* * * * *